United States Patent [19]
Fain et al.

[11] Patent Number: 5,230,336
[45] Date of Patent: Jul. 27, 1993

[54] METHOD AND APPARATUS FOR IMPEDANCE BASED AUTOMATIC PULSE DURATION ADJUSTMENT FOR DEFIBRILLATION SHOCK DELIVERY

[75] Inventors: Eric Fain; Benjamin Pless, both of Menlo Park, Calif.; Michael Hardage, Kingwood, Tex.

[73] Assignee: Ventritex, Inc., Sunnyvale, Calif.

[21] Appl. No.: 746,430

[22] Filed: Aug. 16, 1991

[51] Int. Cl.$^5$ .............................................. A61N 1/39
[52] U.S. Cl. ..................................................... 607/7
[58] Field of Search .................................. 128/419 D

[56] References Cited

U.S. PATENT DOCUMENTS 3,706,313 12/1972 Milani et al. .................... 128/419 D
4,574,810 3/1986 Lerman .......................... 128/419 D

FOREIGN PATENT DOCUMENTS 0315368 5/1989 European Pat. Off. .
0437104 7/1991 European Pat. Off. .
2070282 9/1981 United Kingdom .

OTHER PUBLICATIONS

"Transthoracic Ventricular Defibrillation in the 100 kg Calf with Symmetrical One-Cycle Bidirectional Rectangular Wave Stimuli" (Schuder, et al) IEEE Transactions on Biomedical Engineering, vol. BME-30, No. 7, Jul. 1983.

Primary Examiner—William E. Kamm
Attorney, Agent, or Firm—Steven M. Mitchell; Mark J. Meltzer

[57] ABSTRACT

An antitachycardia device, either implanted or external, which delivers a fixed pulse width truncated exponential waveform defibrillation shock and automatically adjusts the pulse duration based upon the impedance measured or calculated following a delivered shock. The apparatus operates by measuring or calculating the high voltage system impedance, selecting a pulse width for that impedance value and using a pulse width derived from the selected pulse width for the next defibrillation shock.

22 Claims, 6 Drawing Sheets

| Measured Impedance (ohms) | Monophasic Waveform Suggested Pulse Width (msec) | Biphasic Waveform Suggested Pulse Width (msec) |
|---|---|---|
| < 19 | 3.0 | 3.0/3.0 |
| 20-26 | 4.0 | 4.0/4.0 |
| 27-32 | 5.0 | 5.0/5.0 |
| 33-38 | 6.0 | 6.0/6.0 |
| 39-44 | 7.0 | 7.0/7.0 |
| 45-51 | 8.0 | 8.0/8.0 |
| 52-57 | 9.0 | 9.0/9.0 |
| 58-63 | 10.0 | 10.0/10.0 |
| 64-69 | 11.0 | 11.0/11.0 |
| > 70 | 12.0 | 12.0/12.0 |

Figure 3

METHOD AND APPARATUS FOR IMPEDANCE BASED AUTOMATIC PULSE DURATION ADJUSTMENT FOR DEFIBRILLATION SHOCK DELIVERY

FIELD OF THE INVENTION

This invention relates generally to implantable medical devices and in particular to an implantable defibrillator that automatically adjusts defibrillation pulse duration based on measured impedance following a shock delivery.

BACKGROUND OF THE INVENTION

Ventricular tachyarrhythmias are electrical diseases of the heart which may result in "sudden death".

In one type, ventricular tachccardia, the heart muscle, which comprises the ventricles, contracts rapidly in a coordinated fashion. In another type, ventricular fibrillation, which may be a sequela to ventricular tachycardia, there is very rapid and uncoordinated contraction of individual muscles fibers of the ventricles. These rapid heart rhythms result in inefficient, or in the case of ventricular fibrillation, no blood being pumped from the heart and may result in death unless an effective intervention is applied within minutes.

Supraventricular tachyarrhythmias, including atrial fibrillation, atrial flutter, and supraventricular tachycardias, are generally nonlethal arrhythmias that also result in less efficient pumping of blood from the heart, and may result in symptoms of palpitations, pre-syncope and angina.

It is well known in the field of cardiology that these atrial and ventricular tachyarrhythmias can be effectively treated by the application of a sufficiently strong electric shock. Such shocks may be delivered manually by medical personnel via electrodes placed outside the body on the chest wall, or directly on the heart during surgery. Recently, implantable antitachycardia devices have been developed which automatically monitor the heart's rhythm and deliver an electric shock or rapid pacing pulses via implanted electrodes in response to a tachyarrhythmia episode. Likewise, external automatic devices can be used for in and out-of-hospital therapy for ventricular and supraventricular arrhythmias.

Defibrillation output waveforms used by clinically available defibrillators are produced by capacitor discharge. Internal or implantable defibrillators, as well as some external or transthoracic defibrillators, utilize truncated exponential defibrillation waveforms. The waveforms are produced by charging the capacitors to a selected initial voltage and then allowing the capacitors to discharge for a period of time through defibrillation leads placed in or on the body so that current flows through the heart. The rate of capacitor discharge is dependent upon the impedance of the system.

These truncated exponential waveforms can be designed to have either "fixed tilt" or "fixed pulse width". Fixed tilt defibrillators discharge the capacitors from the selected initial voltage until a predetermined final voltage is reached, the "tilt" being the percentage decline in capacitor voltage from its initial value; therefore, the pulse duration varies directly with the system impedance. In contrast, fixed pulse width defibrillators discharge their capacitors for a preselected duration and, as a result, the tilt of the waveform varies inversely with the impedance of the system; low impedances cause the waveform to have a high tilt, while high impedances result in low tilt.

Previous studies (Gold et al., Am Heart J 1979, 98; 207-212; Wessale et al., J Electrocardiology 1980, 13: 359-366; Schuder et al., IEEE Trans Biomed Eng 1983, BME-30: 415-422; Chapman et al., PACE 1988, 11: 1045-1050; Feeser et al., Circulation 1990, 82: 2128-2141) have shown that there is a relationship between the minimum energy or current required for successful defibrillation and the duration of the defibrillation pulse. These experiments demonstrated that the pulse width could be optimized for a given defibrillation waveform and lead configuration. Shorter pulse durations require higher energy to adequately depolarize the myocardium, while longer pulse widths are probably less effective because of their ability to refibrillate the heart.

Some prior art external defibrillators describe adjusting the defibrillation shock based upon impedance (Lerman et al., J Am Cardiol 1988, 12: 1259-1264; Kerber et al., Circulation 1988, 77: 1038-1046). However, these devices do not alter the waveform's pulse duration in response to a previous impedance measurement. The defibrillators delivered damped sinusoidal waveform shocks and either the energy or peak current was adjusted for a transthoracic impedance that was predicted in advance of any shock by passing high frequency alternating current between the defibrillation electrodes. In addition, it is not feasible to use this type of defibrillation waveform or method of predicting interelectrode impedance in an implantable device.

As explained above, fixed pulse width truncated exponential waveforms will have differing tilts depending upon the impedance of the system. Therefore, the most effective pulse width for a defibrillation waveform will change as the impedance of the system changes. This is particularly true when a biphasic waveform is employed. With a biphasic waveform produced from a single capacitor discharge, the initial voltage of the second negative phase is dependent upon the final voltage remaining on the capacitors at the end of the first phase. If the pulse duration of the first phase is too long for a given system impedance, then the tilt of the first phase will be high, resulting in little voltage remaining on the capacitors and a very low energy and less effective negative phase. If the biphasic waveform's pulse duration-impedance mismatch is large enough, it can result in the delivery of a waveform that is effectively monophasic.

Investigations have shown that, for implantable defibrillator systems, the high voltage lead impedance can change dramatically from that measured at the time of implantation. Typically, the impedance decreases initially, reaching its nadir during the first one to two weeks after implantation, and then gradually increases and stabilizes. In addition, the impedance may change significantly with changes in the patient's clinical course, such as a new myocardial infarction, scarring, worsening or improving heart failure, pericarditis or pericardial effusion. Changes in the defibrillation lead system, including shifting of position, dislodgment or damage, may also cause a large impedance change. These changes in impedance could result in delivery of a preselected fixed pulse width defibrillation waveform which is unable to successfully terminate a tachyrhythmia episode.

It would, therefore, be highly desirable to have available a method of automatically adjusting the pulse duration of a subsequent fixed pulse width truncated exponential defibrillation waveform based upon the impedance measured or calculated following a delivered shock.

SUMMARY OF THE INVENTION

The present invention provides an antitachyarrhythmia device, either implanted or used externally, which delivers a fixed pulse width truncated exponential waveform defibrillation shock and automatically adjusts the pulse duration based upon the impedance measured or calculated following a delivered shock. This method is primarily intended for use with a device which monitors the heart's rhythm and automatically delivers therapy upon diagnosing a tachyarrhythmia, but can also be used with a manually triggered device. It may be used with a variety of defibrillation waveforms including monophasic, biphasic or triphasic, when delivering therapy for supraventricular or ventricular arrhythmias.

In one embodiment, the method comprises the steps of: diagnosing an arrhythmia; delivering defibrillation therapy using the current pulse width setting; measuring or calculating the high voltage system impedance; selecting a suggested pulse width for that impedance value from a pulse width table; and using that suggested pulse width for the next defibrillation shock.

The method may also include an additional step of determining whether or not the delivered defibrillation waveform had an initial voltage greater than a predetermined minimum value. In this case, the method comprises the steps of: diagnosing an arrhythmia; delivering defibrillation therapy using the current pulse width setting; measuring or calculating the high voltage system impedance; determining whether or not the delivered defibrillation waveform had an initial voltage greater than a predetermined minimum value; only allowing the pulse width to be adjusted if the initial voltage was greater than that minimum value; selecting a suggested pulse width for that impedance value from a pulse width table; and using that suggested pulse width for the next defibrillation shock. This method prevents the pulse width from being adjusted after low voltage shocks, in which the impedance measurement is less accurate or different from higher voltage shocks, where optimization is important.

The method may also include an additional step of averaging the current pulse width with the suggested pulse width. This average may have either the current pulse width and the suggested pulse width weighted equally or unequally. In this case, the method comprises the steps of: diagnosing an arrhythmia; delivering defibrillation therapy using the current pulse width setting; measuring or calculating the high voltage system impedance; selecting a suggested pulse width for that impedance value from a pulse value table; averaging the current and suggested pulse widths in a weighted or nonweighted manner; and using that averaged pulse width for the next defibrillation shock. This decreases the reactivity of the pulse width adjustment in response to a single impedance measurement.

The method may also include an additional step of adjusting the pulse width by differing degrees based upon whether or not the defibrillation shock was successful in terminating the arrhythmia. In this case, the method comprises the steps of: diagnosing an arrhythmia; delivering defibrillation therapy using the current pulse width setting; measuring or calculating the high voltage system impedance; selecting a suggested pulse width for that impedance value from a pulse value table; determining whether or not the defibrillation shock was successful in terminating the tachyarrhythmia; adjusting pulse width differently based upon whether or not the shock was successful or unsuccessful; and using that pulse width for the next defibrillation shock. This method changes the reactivity of the pulse width adjustment depending upon the outcome of the defibrillation therapy.

A better understanding of the features and advantages of the present invention will be obtained by reference to the following detailed description of the invention and accompanying drawings which set forth illustrative embodiments in which the principles of the invention are utilized.

BRIEF DESCRIPTION OF THE DRAWINGS

FIG. 3 is an example of a table of suggested pulse widths, based on a 150 microfarad source capacitance, for a range of measured impedance values utilizable with the device shown in FIG. 1.

DETAILED DESCRIPTION OF THE PREFERRED EMBODIMENT

Figure 1:
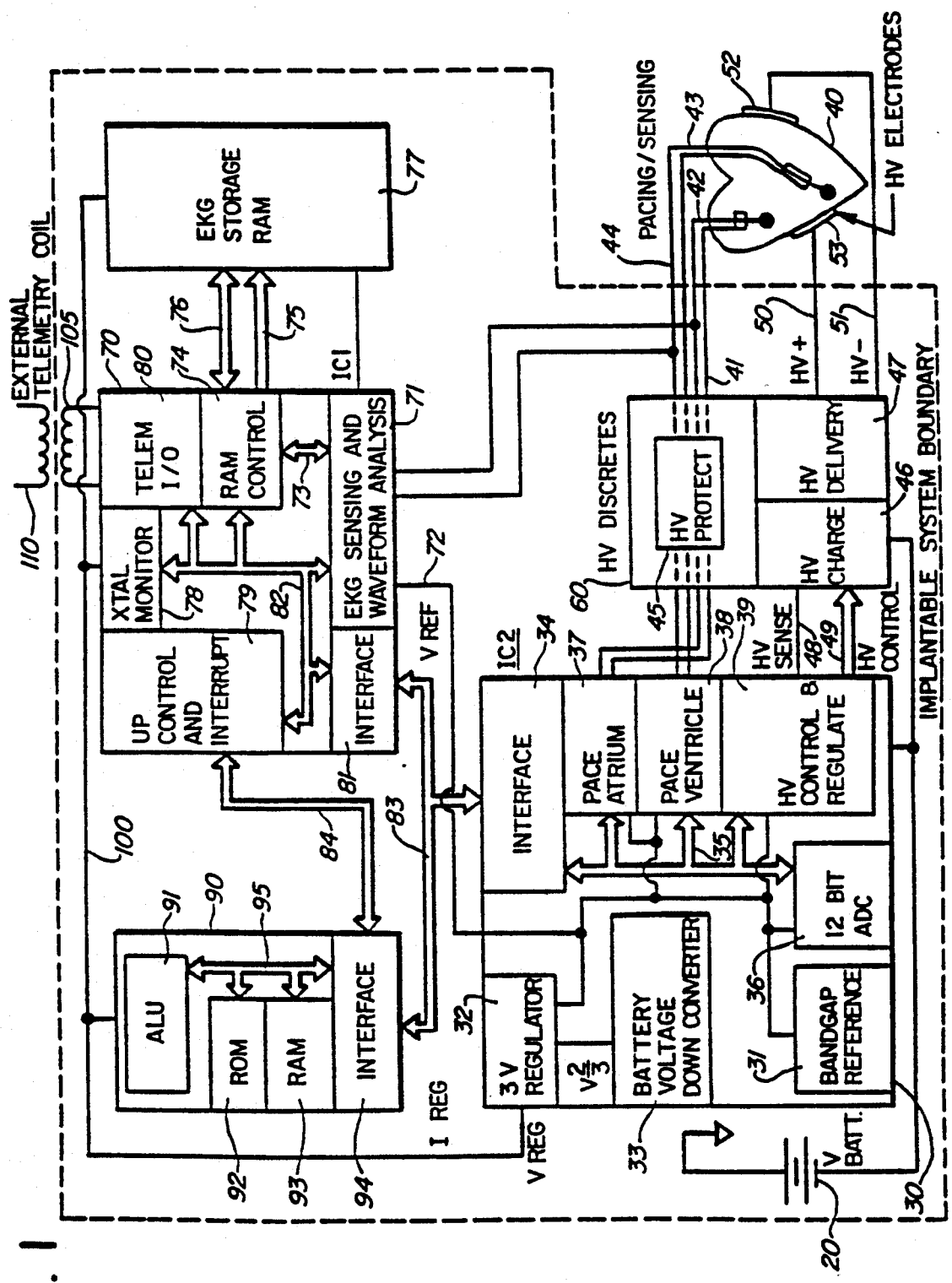
FIG. 1 is a block diagram illustrating an implantable pacer/defibrillator system constructed in accordance with the principles of the present invention.

FIG. 1 shows a block diagram of an implantable defibrillator system 10 which integrates the functions of antitachycardia pacing, cardioversion, defibrillation and demand bradycardia pacing.

The implantable defibrillator system 10 includes four integrated circuits (IC) and a set of high voltage discrete components.

A battery 20 produces a positive voltage with respect to ground that varies from about 6.4 volts when new, to 5.0 volts at the end of service. The battery 20 directly powers integrated circuit 30 and the high voltage discretes 60.

Integrated circuit 30 contains a band-gap reference circuit 31 that produces 1.235 volts and 3 volt regulator 32 that powers a microprocessor 90, integrated circuit 70, and an ECG storage RAM 77 through line 100. The 3 volt regulator runs off of a switched capacitor V ⅔ battery voltage down converter 33 for improved efficiency. The microprocessor 90 communicates with integrated circuit 30 through a data and address bus 83 and an on-chip interface 34 that contains chip-select, address decoding and data bus logic typically used with microprocessor peripherals. The internal bus 35 of integrated circuit 30 allows the microprocessor 90 to control a general purpose 12 bit analog-to-digital converter (ADC) 36, the atrial pace circuits 37, the ventricular pace circuits 38, and the HV control and regulate block 39.

The ADC 36 is used by the microprocessor 90 to measure the battery and other diagnostic voltages within the system 10. The atrial pace circuits 37 include a digital-to-analog converter (DAC) that provides the ability to pace at regulated voltages. It communicates with the atrium of a heart 40 through two lines. One line 41 is a switchable ground; the other line 42 is the pacing cathode and is also the input to the atrial sense amplifier, as will be described in greater detail below.

The ventricular pace circuits 37 include a DAC that provides the ability to pace at regulated voltages. It communicates with the ventricle of the heart 40 through two lines. One line 43 is a switchable ground; the other line 44 is the pacing cathode and is also the input to the ventricular sense amplifier, as will be described in greater detail below.

Both the atrial and ventricular pace lines pass through high voltage protection circuits 45 to prevent the defibrillation voltages generated by the system 10 from damaging the pacing circuits 37, 38.

The high voltage (HV) control and regulate block 39 on integrated circuit 30 is used by the microprocessor 90 to charge a high voltage capacitor included in the HV charge block 46 to a regulated voltage, and then to deliver the defibrillation pulse to the heart 40 through the action of switches in the HV delivery block 47. An HV sense line 48 is used by the HV regulation circuits 39 to monitor the defibrillation voltage during charging. An HV control bus 49 is used by the HV control circuits 39 to control the switches in the HV delivery block 47 for delivering the defibrillation pulse to the electrodes 52, 53 through lines 50 and 51.

Integrated circuit 70 is another microprocessor peripheral that provides timing, interrupt, telemetry, ECG storage, and sensing functions. A dual channel electrogram sensing and waveform analysis section 71 interfaces with the atrium and ventricle of the heart 40 through lines 42 and 44, respectively. The sensed electrogram is amplified and digitized. The amplifiers contained in sensing/analysis section 71 have multiple gain settings that are under microprocessor control for maintaining an automatic gain control (AGC). Features such as peak voltage and complex width are extracted by the waveform analysis circuits 71 for the microprocessor 90 to use in discriminating arrhythmias from normal sinus rhythm. The voltage reference 31 from integrated circuit 30 is used by the digitizer circuit 71 in the usual fashion, and is supplied by line 72.

The digitized ECG is provided to the RAM controller 74 through a bus 73. The RAM controller sequences through the addresses of a static EKG storage RAM 77 to maintain a pretrigger area, and produces a post trigger area upon command from the microprocessor 90.

The crystal and monitor block 78 has a 100 KHz crystal oscillator that provides clocks to the entire system. The monitor is a conventional R-C oscillator that provides a back-up clock if the crystal should fail.

The microprocessor 90 communicates with integrated circuit 70 through two buses, 83 and 84. One bus 83 is a conventional data and address bus and goes to an on-chip interface 81 that contains chip select, address decoding and data bus drivers typically used with microprocessor peripherals. The other bus 84 is a control bus. It allows the microprocessor 90 to set up a variety of maskable interrupts for events like timer timeouts and sense events. If an interrupt is not masked, and the corresponding event occurs, an interrupt is sent from integrated circuit 70 to the microprocessor 90 to alert it of the occurrence. On integrated circuit 70, the microprocessor control and interrupt section 79 contains microprocessor controllable timers and interrupt logic.

The system 10 can communicate with the outside world through a telemetry interface 80. A coil 105 is used in a conventional fashion to transmit and receive pulsed signals. The telemetry circuits 80 decode an incoming bit stream from an external coil 110 and hold the data for subsequent retrieval by the microprocessor 90. When used for transmitting, the telemetry circuit 80 receives data from the microprocessor 90, encodes it, and provides the timing to pulse the coil 105. The communication function is used to retrieve data from the implanted device and to change the modality of operation if required.

The microprocessor 90 is of conventional architecture comprising an algorithmic logic unit (ALU) 91, a ROM 92, a RAM 93 and interface circuits 94. The ROM 92 contains the program code that determines the operation of the device. The RAM 93 is used to modify the operating characteristics of the device as regards modality, pulse widths, pulse amplitudes, and so forth. Diagnostic data is also stored in the RAM 93 for subsequent transmission to the outside world. The ALU 91 performs the logical operations directed by the program code in the ROM.

FIGS. 2, 4, 5 and 6 depict four different embodiments of the present invention, which are provided for purposes of illustration only. One skilled in the art will readily recognize from the following discussion that alternative embodiments of these embodiments may be employed without departing from the principles of the invention.

Figure 2:
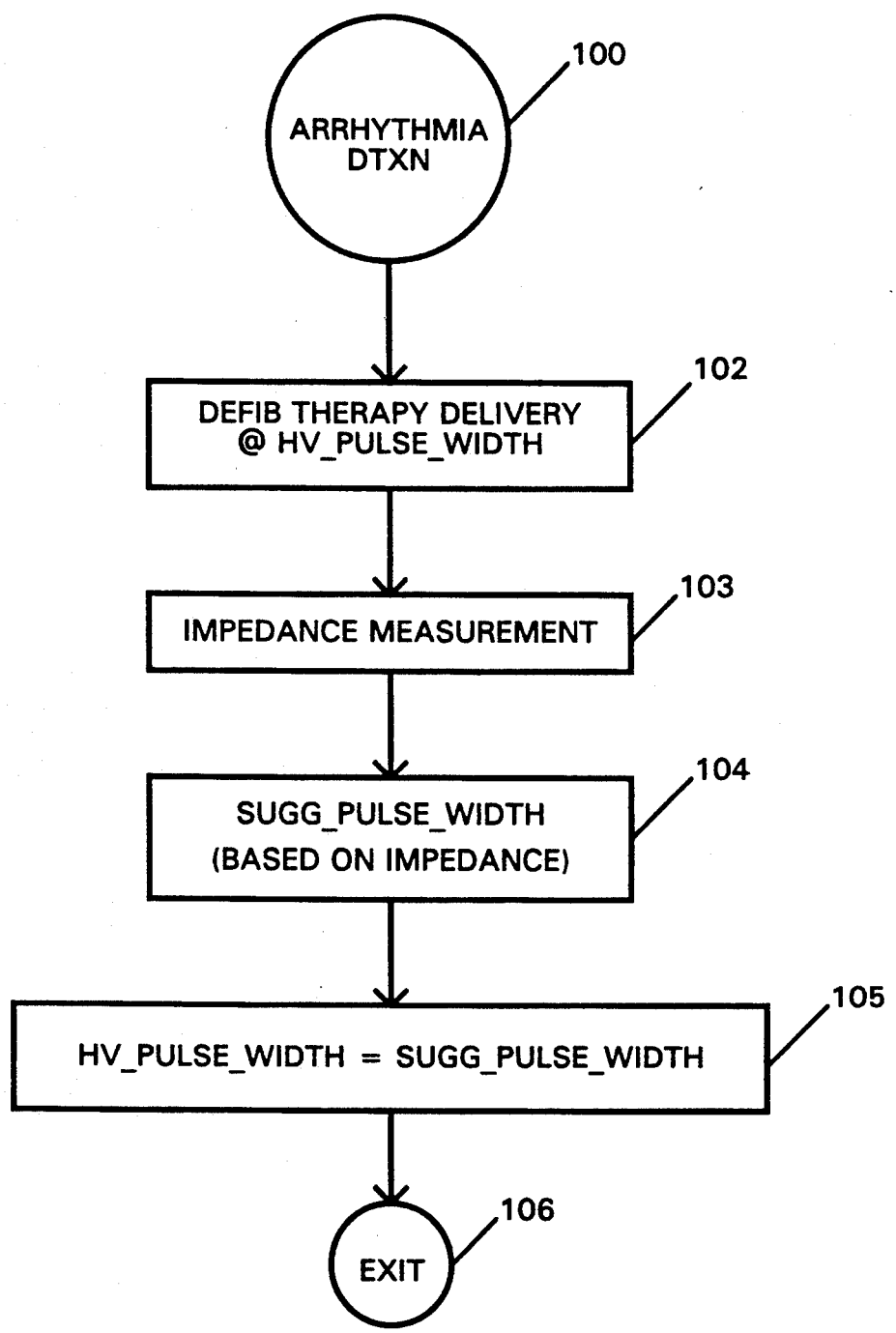
FIG. 2 is a flow chart illustrating an impedance-based automatic pulse width adjustment algorithm utilizable with the device shown in FIG. 1.

The flow diagram shown in FIG. 2 represents a method of automatically adjusting the pulse duration of a fixed pulse width truncated exponential waveform defibrillation shock based upon the impedance measured or calculated following a delivered shock. The flow diagram depicts the use of the algorithm by a device which monitors the heart's rhythm, detects and diagnoses the presence of an arrhythmia 10 and automatically delivers defibrillation therapy. The delivery of high voltage therapy 102 may instead be initiated manually. The tachyarrhythmia therapy 102 may have been delivered for either supraventricular tachycardia, atrial fibrillation, ventricular tachycardia or ventricular fibrillation. It should be appreciated that, as the term is used herein, "defibrillation" includes both high and low voltage/energy shocks for either supraventricular tachycardia, atrial fibrillation, ventricular tachycardia or ventricular fibrillation.

After delivery of the defibrillation shock, the impedance of the high voltage system is measured 103. An optimal pulse width for this impedance value can then be chosen from a predetermined table of suggested pulse durations 104, and the pulse width for the subsequent defibrillation shock changed to this value 105.

An example of such a table is provided in FIG. 3. In this case, the values have been chosen so that the waveform has a relatively constant tilt over a wide range of impedances, assuming a source capacitance of 150 microfarads. In addition, at both very high and very low impedance values, the pulse width has been limited to maximum and minimum durations in order to maintain an effective waveform. Suggested pulse widths in the FIG. 3 table are given for a monophasic waveform, as well as for a biphasic waveform that has equal positive and negative phase durations. Other biphasic or multiphasic waveforms, that have unequal phase durations, could also be used in such a table by, for example, keeping the ratio of the phase durations constant as the total pulse width varies with the measured impedance, or by defaulting to equal pulse durations if the pulse width is adjusted.

Figure 4:
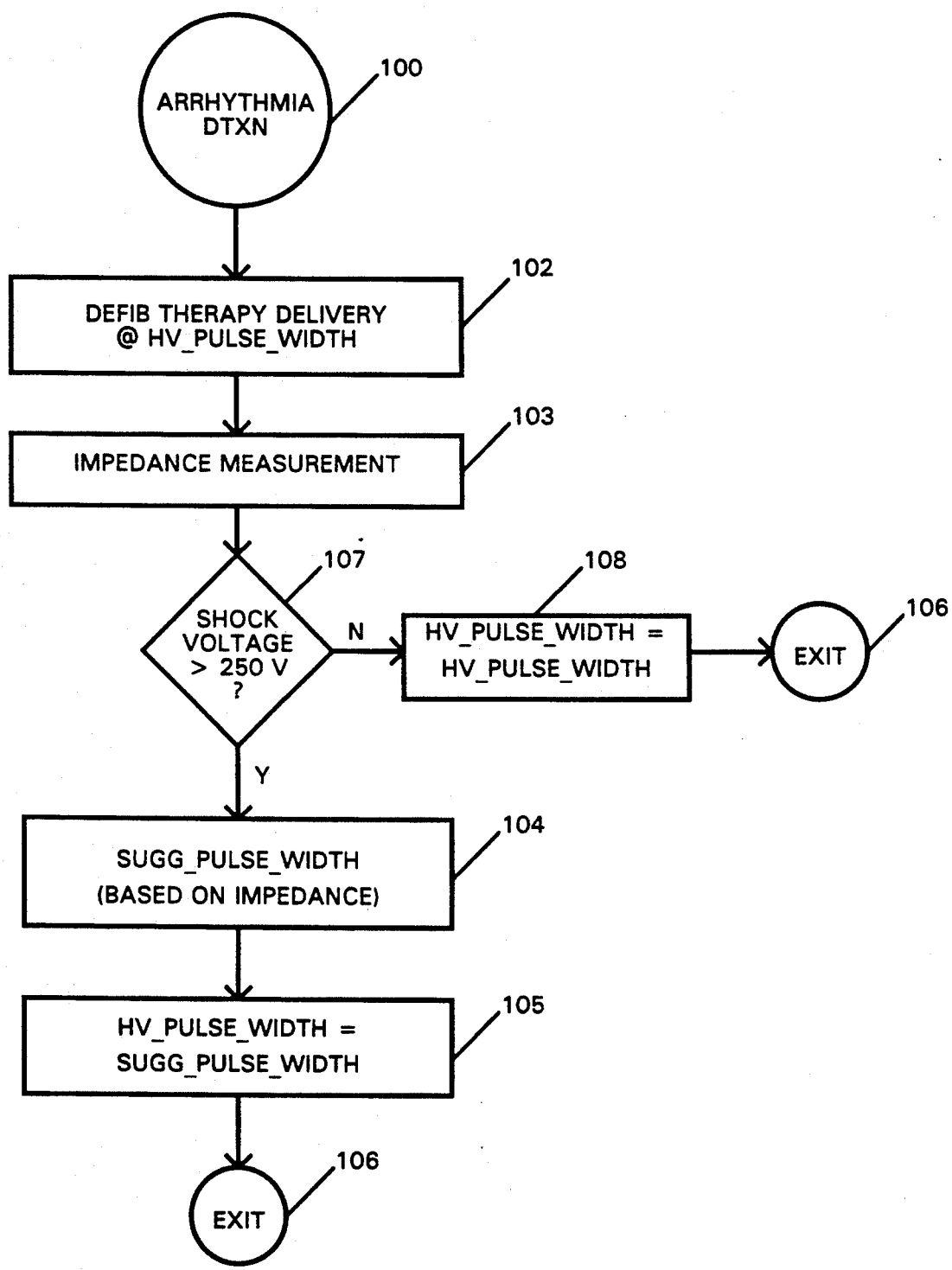
FIG. 4 is a flow chart illustrating an impedance-based automatic pulse width adjustment algorithm which includes an additional step of determining whether or not the delivered defibrillation waveform had an initial voltage greater than a predetermined minimum value.

FIG. 4 shows an alternative embodiment of the present invention such that an additional test is performed to determine whether or not the pulse width should be adjusted based upon the impedance measurement. This test 107 determines whether or not the delivered defibrillation waveform had an initial voltage greater than a predetermined minimum value.

Impedance is, in a non-linear manner, partially dependent upon the initial voltage of the shock. As a result, low voltage shocks may over-estimate the impedance for higher voltage shocks.

In the FIG. 4 embodiment, a value of 250 volts is shown as an example of this minimum value, but of course this can vary with the type of device and defibrillation lead system that is used. If the initial voltage of the defibrillation shock is determined to have been greater than this predetermined value, then the pulse width is adjusted as in the method described above in conjunction with FIG. 2. However, if this condition is not satisfied, then the pulse width is left unchanged 8.

Figure 5:
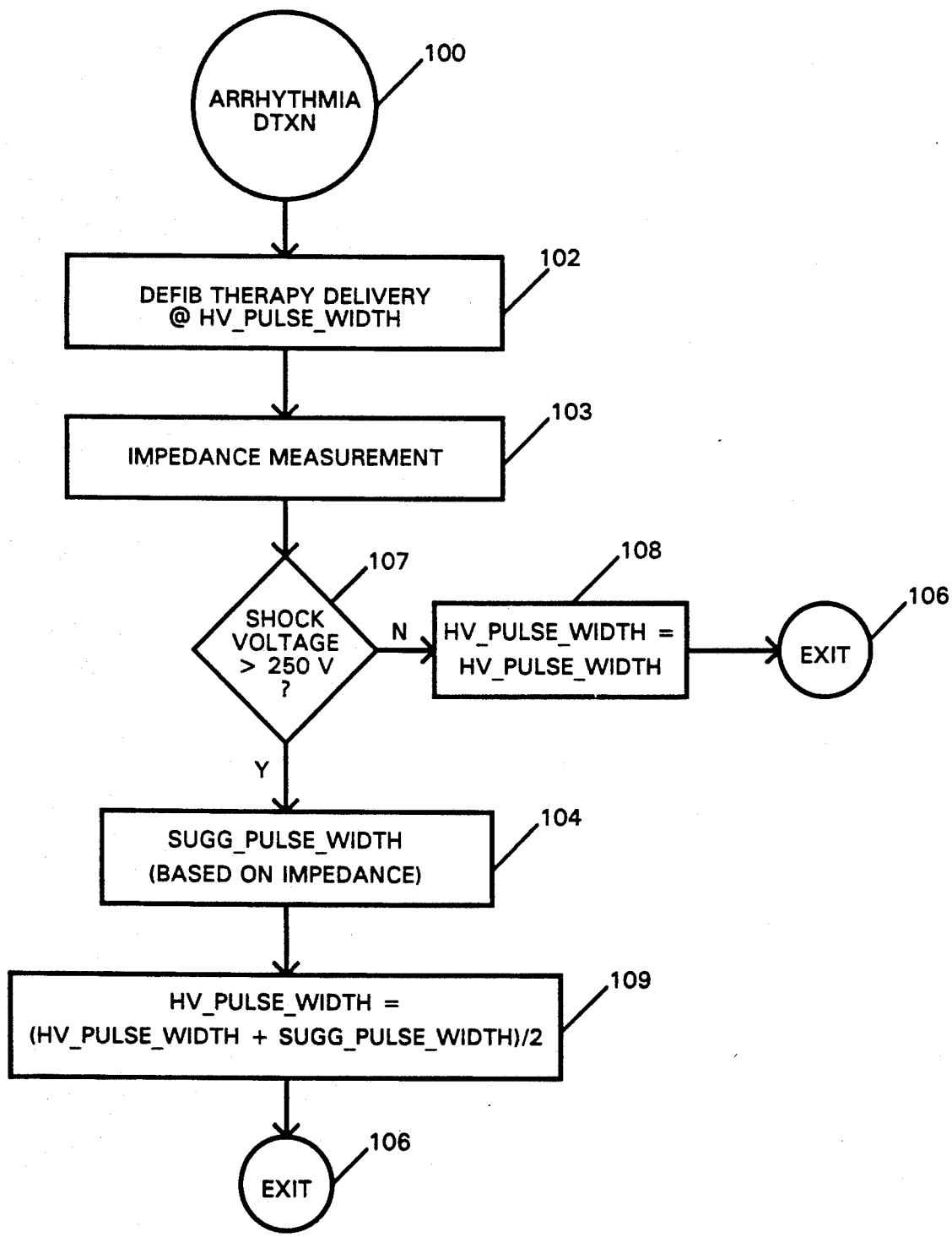
FIG. 5 is a flow chart illustrating an impedance-based automatic pulse width adjustment algorithm which includes an additional step of averaging the current pulse width with the suggested pulse width.

FIG. 5 shows a further alternative embodiment of the present invention wherein the defibrillation waveform's pulse width is adjusted to an average of the current pulse width and the suggested pulse width 109, instead of being set to the suggested pulse width. This average may have either the current pulse width and the suggested pulse width weighted equally, as shown in FIG. 5, or weighted unequally. This averaging may be used in a method independent of the use of step 107. This decreases the reactivity of the pulse width adjustment in response to a single impedance measurement.

Figure 6:
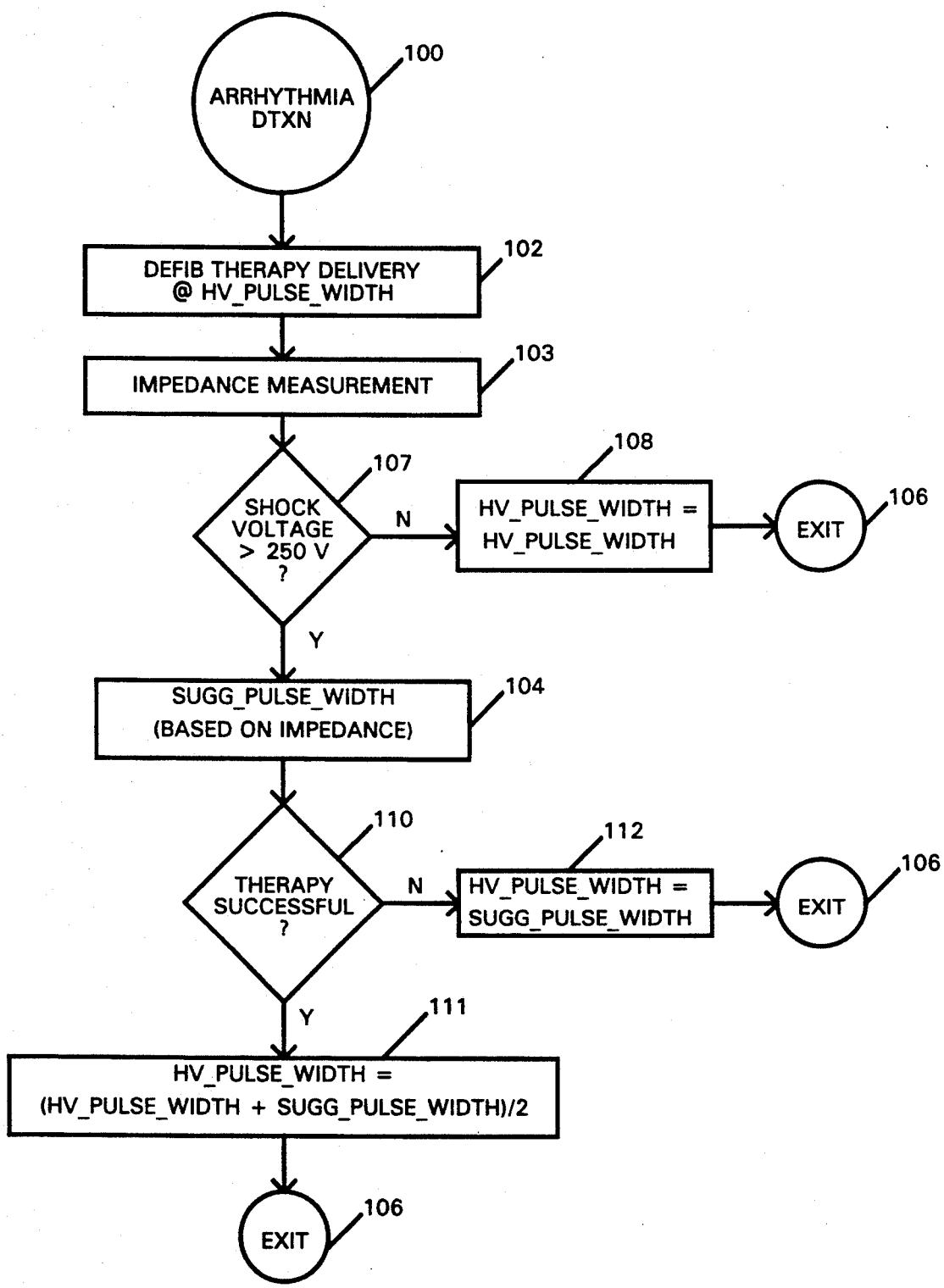
FIG. 6 is a flow chart illustrating an impedance-based automatic pulse width adjustment algorithm which includes an additional step of adjusting the pulse width by differing degrees based upon whether or not the defibrillation shock was successful in terminating the arrhythmia.

FIG. 6 shows a further alternative embodiment of the present invention which includes an additional step wherein the defibrillation waveform's pulse width is adjusted differently based upon whether or not the defibrillation shock was successful in terminating the arrhythmia 110. As an example, FIG. 6 shows a method whereby the pulse width is set equal to the suggested pulse width if the shock is unsuccessful 112 (i.e., more reactive), while it is set to an equally weighted average of the current and suggested pulse widths if the therapy is successful 111 (i.e., less reactive). Another variation could be to only adjust the pulse width following unsuccessful shocks. This step may be used in a method independent of the use of step 107 or averaging of the current and suggested pulse widths.

It should be understood that various alternatives to the embodiment of the invention described herein may be employed in practicing the invention. For example, while the invention is disclosed above in the context of an implantable device, the concepts of the invention are also applicable to manual delivery systems. It is intended that the following claims define the scope of the invention and that structures and methods within the scope of these claims and their equivalents be covered thereby.

What is claimed is:

1. A method of delivering a preselected pulse width defibrillation shock to a heart and automatically adjusting the pulse width for a subsequent shock based upon the impedance of the heart, the method comprising the sequential steps of:
    (a) diagnosing an arrhythmia of the heart;
    (b) delivering a defibrillation shock to the heart using a current pulse width value;
    (c) determining the impedance of the heart;
    (d) selecting a pulse width corresponding to the impedance of the heart; and
    (e) delivering a subsequent defibrillation shock having a pulse width derived from the selected pulse width.

2. A method of delivering a selected pulse width defibrillation shock to a heart based on the impedance of the heart, the method comprising:
    (a) determining the impedance of the heart;
    (b) comparing the impedance of the heart with a predetermined criteria to determine whether the impedance of the heart meets the predetermined criteria;
    (c) selecting a pulse width corresponding to the impedance of the heart only if the impedance of the heart meets the predetermined criteria; and
    (d) delivering a defibrillation shock having a pulse width derived from the selected pulse width.

3. A method of delivering a selected pulse width defibrillation shock to a heart based on the impedance of the heart, the method comprising:
    (a) determining the impedance of the heart;
    (b) selecting a pulse width corresponding to the impedance of the heart;
    (c) averaging the selected pulse width and a previously-used pulse width; and
    (d) delivering a defibrillation shock having a pulse width derived from the average pulse width.

4. A method of delivering a preselected pulse width defibrillation shock to a heart and automatically adjusting the pulse width for a subsequent shock based upon the impedance of the heart, the method comprising the sequential steps of:
    (a) diagnosing an arrhythmia of the heart;
    (b) delivering a defibrillation shock to the heart, the shock having a preselected pulse width value;
    (c) determining the impedance of the heart;
    (d) selecting a pulse width corresponding to the impedance of the heart;
    (e) averaging the preselected pulse width and the selected pulse width; and
    (f) delivering a subsequent defibrillation shock having the average pulse width.

5. A method as in claim 4 wherein said averaging step comprises the step of calculating a weighted average.

6. A method of delivering a selected pulse width defibrillation shock to a heart based on the impedance of the heart, the method comprising:
    (a) determining the impedance of the heart;
    (b) selecting a pulse width corresponding to the impedance of the heart;
    (c) delivering a defibrillation shock having a pulse width derived from the selected pulse width;
    (d) determining whether or not the defibrillation shock was successful in terminating the arrhythmia;

(e) adjusting the pulse width differently based upon whether or not the defibrillation shock was successful; and (f) delivering a subsequent defibrillation shock having the adjusted pulse width.

7. A method of delivering a preselected pulse width defibrillation shock to a heart and automatically adjusting the pulse width for a subsequent shock based upon the impedance of the heart following a delivered defibrillation shock, the method comprising:

(a) diagnosing an arrhythmia;

(b) delivering a defibrillation shock having the preselected pulse width;

(c) determining the impedance of the heart;

(d) selecting a pulse width corresponding to the impedance of the heart;

(e) determining whether or not the defibrillation shock was successful in termination the arrhythmia;

(f) adjusting the selected pulse width differently based upon whether or not the defibrillation shock was successful; and (g) delivering a subsequent defibrillation shock having the adjusted pulse width.

8. Apparatus for delivering an adjustable pulse width defibrillation shock to a heart based on the impedance of the heart, the apparatus comprising:

(a) means connected to the heart for determining the impedance of the heart;

(b) selection means connected to the impedance determining means for selecting a pulse width corresponding to the impedance of the heart; and (c) means connected to the heart for delivering a defibrillation shock having a pulse width derived from the selected pulse width.

9. Apparatus for delivering an adjustable pulse width defibrillation shock to a heart based on the impedance of the heart, the apparatus comprising:

(a) means connected to the heart for determining the impedance of the heart;

(b) comparison means connected to the impedance determining means for comparing the impedance of the heart with a predetermined criteria to determine whether the impedance of the heart meets the predetermined criteria;

(c) selection means connected to the comparison means for selecting a pulse width corresponding to the impedance of the heart only if the impedance of the heart meets the predetermined criteria; and (d) means connected to the heart for delivering a defibrillation shock having a pulse width derived from the selected pulse width.

10. Apparatus for delivering a predetermined pulse width defibrillation shock to a heart and automatically adjusting the pulse width for a subsequent shock based upon the impedance of the heart following a delivered defibrillation shock, the apparatus comprising:

(a) diagnostic means connected to the heart for diagnosing an arrhythmia;

(b) delivery means connected to the heart for delivering a defibrillation shock having a current pulse width;

(c) means connected to the heart for measuring the impedance of the heart;

(d) comparison means connected to the impedance measuring means for comparing the impedance of the heart with a predetermined criteria to determine whether the impedance of the heart meets the predetermined criteria; and (e) selection means connected to the comparison means for selecting a pulse width corresponding to the impedance of the heart only if the impedance of the heart meets the predetermined criteria;

(f) whereby the delivery means delivers a subsequent defibrillation shock having a pulse width derived from the selected pulse width.

11. Apparatus for delivering an adjustable pulse width defibrillation shock to a heart based on the impedance of the heart, the apparatus comprising:

(a) means connected to the heart for determining the impedance of the heart;

(b) selection means connected to the impedance determining means for selecting a pulse width corresponding to the impedance of the heart;

(c) averaging means connected to the selection means for averaging a previous pulse width and the selected pulse width; and (d) delivery means connected to the heart for delivering a subsequent defibrillation shock having the average pulse width.

12. Apparatus as in claim 11 wherein the averaging means is adapted to generate a weighted average.

13. Apparatus for delivering a preselected pulse width defibrillation shock to a heart and automatically adjusting the pulse width based upon the impedance of the heart following a delivered defibrillation shock, the apparatus comprising:

(a) diagnostic means connected to the heart for diagnosing an arrhythmia;

(b) delivery means connected to the heart for delivering a defibrillation shock having a current pulse width;

(c) means connected to the heart for determining the impedance of the heart;

(d) selection means connected to the impedance determining means for selecting a pulse width corresponding to the impedance of the heart; and (e) averaging means connected to the selection means for averaging the current pulse width and the selected pulse width;

(f) whereby the delivery means delivers a subsequent defibrillation shock having the average pulse width.

14. Apparatus as in claim 13 wherein the averaging means generates a weighted average.

15. Apparatus for delivering an adjustable pulse width defibrillation shock to a heart based on the impedance of the heart, the apparatus comprising:

(a) means connected to the heart for determining the impedance of the heart;

(b) selection means connected to the selection means and to the heart for delivering a defibrillation shock having a pulse width derived from the selected pulse width;

(c) delivery means connected to the selection means and to the heart for delivering a defibrillation shock having a pulse width derived from the selected pulse width;

(d) diagnostic means connected to the heart for determining whether or not the defibrillation shock was successful in terminating the arrhythmia; and (e) means connected to the delivery means for adjusting the pulse width differently based upon whether or not the defibrillation shock was successful whereby the delivery means delivers a subsequent defibrillation shock having the adjusted pulse width.

16. Apparatus for delivering an adjustable pulse width defibrillation shock to a heart and automatically adjusting the pulse width based upon the impedance of the heart following a delivered defibrillation shock, the apparatus comprising:
   (a) diagnostic means connected to the heart for diagnosing an arrhythmia;
   (b) delivery means connected to the heart for delivering a defibrillation shock having a current pulse width;
   (c) means connected to the heart for determining the impedance of the heart;
   (d) selection means connected to the impedance determining means for selecting a pulse width corresponding to the impedance of the heart; the diagnostic means including means for determining whether or not the defibrillation shock was successful in terminating the arrhythmia; and
   (e) means connected to the delivery means for adjusting the pulse width differently based upon whether or not the defibrillation shock was successful; whereby the delivery means delivers a subsequent defibrillation shock having the adjusted pulse width.

17. A method of delivering a sequence of defibrillation shocks to a patient's heart comprising the steps of:
   (a) diagnosing an arrhythmia of the heart;
   (b) delivering a first defibrillation shock to the heart via a high voltage system, said first shock having a fixed pulse width value;
   (c) determining the impedance of the high voltage system;
   (d) selecting a pulse width for a subsequent defibrillation shock as a function of the determined impedance of the high voltage system; and
   (e) delivering a subsequent defibrillation shock having the selected pulse width.

18. A method of delivering a defibrillation shock to a patient's heart comprising the steps of:
   (a) determining the impedance of the heart and a shock delivery system coupled to the heart;
   (b) selecting a pulse width for said shock as a function of the impedance of the heart and shock delivery system; and
   (c) delivering a defibrillation shock having a pulse width based on said selected pulse width.

19. The method of claim 18 and further including the step of averaging the selected pulse width with a previously-used pulse width to provide the pulse width for delivery of the defibrillation shock.

20. Apparatus for delivering a defibrillation shock to a patient's heart based on the impedance of a high voltage system and the heart, the apparatus comprising:
   (a) means for determining the impedance of the high voltage system and heart;
   (b) means connected to the impedance determining means for selecting a pulse width based on the impedance of the heart; and
   (c) means connected to the heart for delivering through the high voltage system a defibrillation shock having a pulse width derived from the selected pulse width.

21. Apparatus for delivering a defibrillation shock to a heart comprising:
   (a) a high voltage system for delivering a defibrillation shock to the heart having a selected pulse width;
   (b) means for determining the impedance of the high voltage system and the heart;
   (c) means connected to the impedance determining means for comparing the impedance of the high voltage system and the heart with a predetermined criteria to determine whether the impedance of the high voltage system and the heart meets the predetermined criteria;
   (d) selection means connected to the comparing measn for selecting a pulse width based on the impedance of the high voltage system and the heart only if the impedance of the high voltage system and the heart meets the predetermined criteria.

22. Apparatus for delivering a defibrillation shock having a preselected pulse width to a heart and automatically adjusting the pulse width based upon the impedance of the heart and a high voltage system following a delivered defibrillation shock, the apparatus comprising:
   (a) diagnostic means connected to the heart for diagnosing an arrhythmia;
   (b) delivery means including the high voltage system connected to the heart for delivering a defibrillation shock having a first pulse width;
   (c) means for determining the impedance of the heart and the high voltage system;
   (d) selection means connected to the impedance determining means for selecting a second pulse width based on the impedance of the heart and the high voltage system; and
   (e) averaging means connected to the selection means for averaging the first pulse width and the second pulse width;
   (f) whereby the delivery means delivers a subsequent defibrillation shock having the average pulse width.

* * * * *